United States Patent
Romaschin (12)

(10) Patent No.: US 6,270,725 B1
(45) Date of Patent: Aug. 7, 2001

(54) DIAGNOSTIC KIT FOR ASSAYING SUCROSE IN PHYSIOLOGICAL FLUIDS

(76) Inventor: Alex D. Romaschin, 3 Broadfield Drive, Etobicoke, Ontario (CA), M9C 1L4

( * ) Notice: Subject to any disclaimer, the term of this patent is extended or adjusted under 35 U.S.C. 154(b) by 0 days.

(21) Appl. No.: 09/037,977

(22) Filed: Mar. 9, 1998

(51) Int. Cl.$^7$ .................................................... G01N 31/22
(52) U.S. Cl. .............................. 422/61; 436/63; 436/808; 436/813; 436/94; 422/58
(58) Field of Search ....................... 422/56, 61; 436/808, 436/63, 811, 813, 93–94

(56) References Cited

U.S. PATENT DOCUMENTS

| | | | |
|---|---|---|---|
| 3,754,864 | * | 8/1973 | Gindler .................................... 422/56 |
| 5,364,765 | * | 11/1994 | Abbott .................................... 435/26 |
| 5,605,840 | | 2/1997 | Meddings et al. ...................... 436/94 |
| 5,620,899 | | 4/1997 | Meddings et al. ...................... 436/63 |

OTHER PUBLICATIONS

Donald's Illustrated Medical Dictionary, 24th edition by W.B. Saunders Company, p.861, 1965.*
In Vitro Diagnostic Products For Human Use, Fed. Reg., vol. 39, No. 126, pp. 24, 136–24, 147 (1974).
Sekin, S., "Enzymatic Determination of Glucose, Fructose, and Sucrose in Tobacco", Tobacco International, vol. 181, Jul. 1979, pp. 27–29.

* cited by examiner

*Primary Examiner*—Lyle A. Alexander
(74) *Attorney, Agent, or Firm*—Fitzpatrick, Cella, Harper & Scinto

(57) ABSTRACT

This invention provides a kit and a method for detecting sucrose in physiological fluids and said method. The kit comprises: (a) a solid mixture comprising ATP, NAD, hexokinase, G-6-PDH, and a buffer; which, after reconstitution with water, results in a solution having a pH in the range from about 7 to about 8; and (b) a solid mixture comprising ATP, NAD, hexokinase, G-6-PDH, invertase, and a buffer; which, after reconstitution with water, results in a solution having a pH in the range from about 7 to about 8.

11 Claims, No Drawings

DIAGNOSTIC KIT FOR ASSAYING SUCROSE IN PHYSIOLOGICAL FLUIDS

BACKGROUND OF THE INVENTION

1. Field of the Invention

This invention relates to a diagnostic kit and a method for determining the concentration of sucrose in a sample of a physiological fluid. The kit and method are useful in connection with a method for the non-invasive detection of gastric damage.

2. Related Background Art

Stomach ulcers can pose a serious health threat as, in many instances, ulcers are asymptomatic. Since stomach ulcers can develop and be present without any symptoms, the damage brought about by ulcers to the stomach and the bleeding associated with such ulcers can be a serious, and possibly fatal health risk.

Traditional methods for detecting gastric ulcers include endoscopy, barium meal followed by x-rays, and radiolabeled detecting agents. Endoscopy causes patient discomfort, requires anesthesia, and must generally be performed in a clinic or a hospital. X-rays and radiolabeled detecting agents have the common disadvantage of exposing the patient to radiation. In addition, all of these procedures require a skilled evaluation of the results in order to properly diagnose the patient's condition.

A method for detection of gastric epithelial damage, particularly ulcers and lesions in the stomach, using non-invasive, non-radioactive and non-x-ray techniques or procedures is disclosed in U.S. Pat. No. 5,620,899. The method of this reference employs a disaccharide which can be orally administered to a patient, which does not transport across cell membranes, which is metabolized within the small intestine to its monosaccharide components, and which is not broken down elsewhere in the body. Damage to the gastric epithelium will allow the disaccharide to enter the blood without being metabolized. Hence, the disaccharide will appear in the blood or urine to an extent that can be correlated with the extent of gastric epithelial damage. Typically, the disaccharide is administered to a patient, followed by collection of blood or urine, which is assayed for the disaccharide. The use of sucrose in particular as a diagnostic marker in detection of gastric epithelial damage is described in U.S. patent application Ser. No. 08/456,203.

The methodology utilized to evaluate the level of sucrose in the blood or urine in conjunction with the performance of the above-described gastric assay must be useful for analyzing physiological fluids. A hexokinase/glucose-6-phosphate method has been suggested for analysis of glucose in serum, plasma, or urine. United States Department of Health, Education and Welfare, Food and Drug Administration. In Vitro Diagnostic Products for Human Use, Proposed Establishment of Product Class Standard for Detection or Measurement of Glucose, Fed. Regist. Vol. 39, No. 126, 24146 (1974). There is, however, no suggestion of measuring sucrose in physiological fluids.

A method is described in S. Sekin, Tobacco International, Vol. 181, 27–27 (1979) for determination of sucrose in tobacco. This method converts glucose in an aliquot of a tobacco sample to 6-phosphogluconate, with concomitant production of NADH, by addition of ATP, hexokinase, glucose-6-phosphate dehydrogenase and NAD. An absorbance measurement at 340 nm is used to quantify the NADH, and hence the endogenous glucose. Another aliquot is treated with invertase, ATP, hexokinase, glucose-6-phosphate dehydrogenase and NAD. The invertase cleaves the sucrose to glucose and fructose. The glucose produced from cleavage, along with the glucose initially present in the sample, is converted to 6-phosphogluconate, producing NADH. An absorbance measurement at 340 nm quantifies NADH, and hence total glucose. The difference between total glucose and endogenous glucose gives the molar amount of sucrose present. However, there is no suggestion that this method would be compatible with analyzing sucrose in complex physiological fluids. In addition, the reagents used for the analysis are non-stabilized solutions which cannot be stored or transported for long periods of time.

A method suitable for determination of sucrose in physiological fluids would be highly desirable, as would a diagnostic kit containing the necessary reagents preformulated for use in such a method.

SUMMARY OF THE INVENTION

This invention is directed to a kit for use in a diagnostic method for detecting sucrose in physiological fluids. The kit comprises: (a) a first container of a solid first reagent mixture comprising ATP, NAD, hexokinase, G-6-PDH, and a buffer; which, after reconstitution with a specified amount of water, results in a first reagent solution comprising (i) ATP in a concentration in the range from about 0.5 mM to about 5.0 mM, (ii) NAD in a concentration in the range from about 0.5 mM to about 3.0 mM, (iii) hexokinase in a concentration in the range from about 200 U/L to about 2,000 U/L, and (iv) G-6-PDH in a concentration in the range from about 500 U/L to about 2,500 U/L, the first reagent solution having a pH in the range from about 7 to about 8; and (b) a second container of a solid second reagent mixture comprising ATP, NAD, hexokinase, G-6-PDH, invertase, and a buffer; which, after reconstitution with a specified amount of water, results in a second reagent solution comprising (i) ATP in a concentration in the range from 0.0 mM to about 5.0 mM, (ii) NAD in a concentration in the range from 0.0 mM to about 3.0 mM, (iii) hexokinase in a concentration in the range from 0 U/L to about 2,000 U/L, (iv) G-6-PDH in a concentration in the range from 0 U/L to about 2,500 U/L, and (v) invertase in a concentration in the range from about 50 kU/L to about 500 kU/L, the second reagent solution having a pH in the range from about 7 to about 8. The kit may also contain a sucrose solution as a standard, and at least one lyophilized urine control sample.

The invention is also directed to a diagnostic method for detecting sucrose in physiological fluids that may be performed with the above-described kit. The method comprises the steps of (a) treating a sample of physiological fluid with ATP, NAD, hexokinase, and G-6-PDH in amounts effective to substantially convert any glucose present in the sample to 6-phosphogluconate; (b) determining an absorbance of a solution formed in step (a) at about 340 nm; (c) treating the solution formed in step (a) with invertase, ATP, NAD, hexokinase, and G-6-PDH in amounts effective to substantially convert any glucose formed from sucrose present in the sample to 6-phosphogluconate; (d) determining an absorbance of a solution formed in step (c) at about 340 nm; and (e) calculating a sucrose concentration from the difference between the absorbance measured in step (b) and the absorbance measured in step (d).

A variation of the method comprises the steps of: (a) treating a first sample of the fluid with ATP, NAD, hexokinase, and G-6-PDH in amounts effective to substantially convert any glucose present in the sample to 6-phosphogluconate; (b) determining an absorbance of a solution formed in step (a) at about 340 nm; (c) treating a second sample of the fluid with invertase, ATP, NAD, hexokinase, and G-6-PDH in amounts effective to substantially convert any glucose present in the sample and glucose formed from sucrose present in the sample to 6-phosphogluconate; (d) determining an absorbance of a solution formed in step (c) at about 340 nm; and (e) calculating a sucrose concentration from the difference between the absorbance measured in step (b) and the absorbance measured in step (d).

DETAILED DESCRIPTION OF THE INVENTION

The following terms are a s defined herein . The term "NAD" indicates the compound nicotinamide adenine dinucleotide. The term "NADH" indicates reduced nicotinamide adenine dinucleotide. The term "ATP" indicates the compound adenosine triphosphate. The term "ADP" indicates the compound adenosine diphosphate. The term "G-6-PDH" indicates the enzyme glucose-6-phosphate dehydrogenase. The term "U" indicates an amount of enzyme measured in units and "U/L" is a measure of enzyme concentration in units per liter. The term "PIPES" indicates the compound 1,4-piperazinebis(ethanesulfonic acid). The term "HEPES" indicates the compound 4-(2 -hydroxyethyl) -1piperazineethanesulfonic acid. The term "TRIS" indicates the compound tris(hydroxymethyl)aminomethane.

The method of this invention measures the concentration of sucrose indirectly by cleaving sucrose to form glucose and fructose, converting glucose to 6-phosphogluconate with concomitant conversion of NAD to NADH, and finally, measuring the absorbance of the sample at about 340 nm, the characteristic absorption maximum of NADH. However, samples of physiological fluids may initially contain glucose (endogenous glucose), which would be converted to 6-phosphogluconate, generating NADH, and elevating the absorbance at about 340 nm above the value corresponding to the amount of sucrose present in the sample. In order to avoid this potential error, the sample is preferably first treated with the reagents necessary to convert any endogenous glucose to 6-phosphogluconate, and a first absorbance reading is taken at about 340 nm. This reading acts as a blank to be subtracted from the final absorbance obtained after cleavage of sucrose and conversion of the resulting glucose to 6-phosphogluconate. conversion of endogenous glucose and a first absorbance reading may be performed on the same sample of the physiological fluid as the sucrose assay, or on a different sample of the same fluid. The use of the same sample is preferred.

The reagents used to convert endogenous glucose in the sample to 6-phosphogluconate are ATP, NAD, hexokinase, and G-6-PDH. The reaction which occurs is as follows:

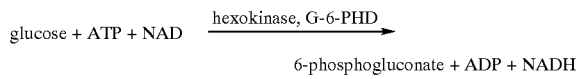

One mole of NADH is produced per mole of endogenous glucose. The absorbance of the sample after treatment with these reagents is measured at about 340 nm to determine the concentration of NADH, which is proportional to the amount of glucose initially present in the sample.

Absorbance may be measured using any ultraviolet spectrophotometer capable of reading absorbance at 340 nm. Such instruments are well known to those skilled in the art. Preferably, a spectrophotometer is used which has a sensitivity of about 0.001 absorbance units at 340 nm, a band width of no more than about 10 nm, stray light of no more than about 0.5%, and a wavelength accuracy better than about 2 nm.

The method is generally carried out at a temperature in the range from about 25° C. to about 37° C., preferably from about 30° C. to about 37° C., and most preferably at about 37° C.

The method of this invention may be carried out either manually or by using an automated instrument. Exemplary automated instruments are Roche Cobas Fara, Roche Cobas Mira (Roche Diagnostics, Nutley, N.J.), Hitachi 704, Hitachi 717, Hitachi 747 (Boerhinger-Mannheim Diagnostics, Tutzingen, Germany), and Ciba Corning 550 Express.

The enzyme invertase, which catalyzes cleavage of sucrose to glucose and fructose, is added to the sample in an a mount sufficient to convert all of the sucrose to glucose. NAD, ATP, and G-6-PDH are also added to convert all of the glucose in the sample to 6-phosphogluconate. If conversion of endogenous glucose and a first absorbance measurement have been performed, the invertase, NAD, ATP, and G-6-PDH may be added to the same sample of physiological fluid on which the first absorbance measurement was performed, or on a different sample of the same fluid. It is preferred to add the reagents to the same sample. If excess NAD, ATP, and G-6-PDH are added in the first step, only invertase is added at this point. The reactions which occur are as follows:

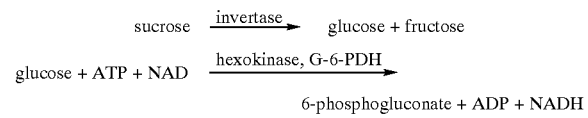

One mole of NADH is produced per mole of glucose derived from sucrose, and hence one mole of NADH is produced per mole of sucrose. The absorbance of the sample is measured at about 340 nm after treatment with these reagents to determine the concentration of NADH, which is proportional to the total amount of glucose. If a first absorbance measurement has been performed, the difference between the absorbance measured at this point and the first absorbance measurement is used to determine the amount of glucose produced from sucrose, and hence the amount of sucrose initially present in the sample. The concentration of sucrose, C, may be expressed as:

$$C=K[A_f-A_i(VCF)]-K[A_{bf}-A_{bi}(VCF)]$$

where: K=calibration factor
 $A_f$=final absorbance of the solution
 $A_i$=initial absorbance of the solution
 $A_{bf}$=final absorbance of the blank
 $A_{bi}$=initial absorbance of the blank
 VCF (volume correction factor)=(sample volume+first reagent volume)/(sample volume+first reagent solution volume+second reagent solution volume)

The kit of this invention is intended for use in the method of this invention for determining the concentration of sucrose in physiological fluids. In the kit, the reagents for the conversion of endogenous glucose to 6-phosphogluconate are packaged together as a first reagent mixture. The mixture may be a first reagent solution which is stabilized. Such a solution may be used neat or further diluted as desired.

Preferably, the mixture is a solid first reagent mixture to be reconstituted with water by the user as a single first reagent solution. The concentrations of the reagents in the first reagent solution must be sufficient to convert all of the endogenous glucose to 6-phosphogluconate. The concentration of ATP may range from about 0.5 mM to about 5.0 mM, preferably from about 1.0 mM to about 3.0 mM. The concentration of NAD may range from about 0.5 mM to about 3.0 mM, preferably from about 1.5 mM to about 2.5 mM. The concentration of hexokinase may range from about 200 U/L to about 2,000 U/L, preferably from about 500 U/L to about 1,000 U/L. The concentration of G-6-PDH may range from about 500 U/L to about 2,500 U/L, preferably from about 1,000 U/L to about 2,000 U/L. The packaged first reagent mixture containing these ingredients also contains a buffer system which stabilizes the pH of the first reagent solution in the range from about 7 to about 8, preferably from about 7.40 to about 7.55. Any physiological buffer system which buffers in this range is suitable, including for example, HEPES, phosphate, PIPES, and TRIS. The preferred buffer system is comprised of PIPES and KOH in a weight ratio of about 2.3:1, respectively. The packaged first reagent mixture may also contain preservatives and stabilizers. Suitable preservatives and stabilizers for use in this invention are well known to those skilled in the art. Preferred preservatives are sodium azide and gentamycin sulfate. The preferred stabilizer is albumin.

At least one magnesium salt may also be added to the mixture as an enzyme cofactor. Magnesium acetate is preferred.

In a preferred embodiment of this invention, the reagents for the conversion of sucrose to 6-phosphogluconate are added as components of a single solution. It is also possible to add a solution containing invertase, followed by a solution containing the reagents for conversion of glucose to 6-phosphogluconate.

The second reagent mixture contains the reagents for the conversion of sucrose to 6-phosphogluconate. Preferably, these reagents are packaged together as a solid second reagent mixture to be reconstituted with water by the user as a single second reagent solution. The second reagent mixture may also be packaged as a stabilized solution. This solution may be used neat or further diluted if desired. The concentrations of the reagents in this second reagent solution must be sufficient to convert all of the sucrose to 6-phosphogluconate. The concentration of invertase may range from about 50 kU/L to about 500 kU/L, preferably from about 300 kU/L to about 400 kU/L. The concentration of ATP may range from 0.0 mM to about 5.0 mM, preferably from about 1.0 mM to about 3.0 mM. The concentration of NAD may range from 0.0 mM to about 3.0 mM, preferably from about 1.5 mM to about 2.5 mM. The concentration of hexokinase may range from 0.0 U/L to about 2,000 U/L, preferably from about 500 U/L to about 1,000 U/L. The concentration of G-6-PDH may range from 0.0 U/L to about 2,500 U/L, preferably from about 1,000 U/L to about 2,000 U/L. The packaged second reagent mixture containing these ingredients also contains a buffer system which stabilizes the pH of the reconstituted second reagent solution in the range from about 7 to about 8, preferably from about 7.40 to about 7.55 at 25° C. The preferred buffer system is comprised of PIPES and KOH in a weight ratio of about 2.3:1, respectively. The packaged solid may also contain preservatives and stabilizers.

When the reagent mixtures are solids or concentrated stabilized solutions, reconstitution or dilution is accomplished by adding water, preferably deionized water. Typically a specified amount of water is added to each reagent mixture to obtain reconstituted reagent solutions with the desired concentration of assay components. Thus, the specified amount of water to be added to each reagent mixture is readily calculated from the levels of assay components that are desired. Likewise, the amount of reagent that is placed in each respective container may be readily calculated after setting a particular amount of water that is to be added. When the reagent mixtures are packaged as solutions, the solutions must carry stabilizers. Such stabilizers are well known to those skilled in the art.

A solid mixture of reagents for conversion of endogenous glucose to 6-phosphogluconate (solid first reagent mixture) is preferably manufactured by mixing the ingredients into water, placing the solution into vials, and then subjecting the vials to a lyophilization procedure to remove the water. The amounts of solution placed into the vials are sufficient to provide the desired concentrations of these reagents after the solids are reconstituted with water in the vials. The lyophilization is carried out using standard techniques well known to those skilled in the art.

A solid mixture of reagents for cleavage of sucrose and conversion of the resulting glucose to 6-phosphogluconate (solid second reagent mixture) is preferably manufactured by adding invertase to the solution prepared in the course of making the solid first reagent mixture. Alternatively, all of the ingredients for the second solution may be mixed into water at one time. In either case, the resulting solution is placed into vials in amounts sufficient to provide the desired concentrations of these reagents after the solids are reconstituted. The water is then removed by lyophilization.

The kit may also contain an aqueous sucrose solution for use as a standard. The sucrose solution contains sucrose at a concentration in the range from about 0.1 mM to about 5 mM, preferably from about 1 mM to about 2 mM. The sucrose solution also contains a preservative to inhibit growth of microorganisms. Suitable preservatives are well known to those skilled in the art.

In addition, the kit may contain at least one solid sample that can be reconstituted with water to form a urine solution containing sucrose. This solution can be used as a control in the analysis. A urine control sample contains the solid components of human urine, sucrose, and a preservative. Preferably, two urine control samples having different concentrations of sucrose are included in the kit. Exemplary preservatives for a urine control sample are boric acid and thymol. Boric acid is the preferred preservative. Preferably, urine control samples are prepared by adding the preservative and a calculated quantity of sucrose to human urine, then removing substantially all of the water, preferably by means of lyophilization.

Another optional part of the kit is a set of instructions for use. The instructions describe the reagents included in the kit, procedures for reconstitution of reagents, stability and storage information, and information regarding the sucrose assay, including sample preparation, instrument settings, and calculations. Preferably the instructions are included in the form of a printed pamphlet.

The examples which follow are intended as illustrations of certain preferred embodiments of the invention, and no limitation of the invention is implied.

EXAMPLE 1

Preparation of Solution R1

The components of the solution (R1) used for conversion of endogenous glucose to 6-phosphogluconate were weighed in the following amounts:

|  | Amount |
| --- | --- |
| ATP | 81.5 g |
| NAD | 93.6 g |
| hexokinase | 42,250 U |
| G-6-PDH | 84,500 U |
| PIPES | 979 g |
| KOH | 426 g |
| magnesium acetate | 28.0 g |
| albumin | 325 g |
| sodium azide | 6.5 g |
| gentamycin sulfate | 1.3 g |

These components were added to approximately 20 liters of deionized water in a 100 liter plastic drum and the contents of the drum mixed with a magnetic stir bar at least 75 mm in length. The mixture was diluted to 32.5 liters and mixed for three hours. A 7.5 liter portion of this solution was set aside for production of solution R2. The remaining 25 liters was used to fill 15 ml glass vials with 5.0–5.1 ml of solution each. The vials were lyophilized at 200 millitorr, using the following temperature program:

| 1 | 2 | 3 | 4 | 5 | 6 |
| --- | --- | --- | --- | --- | --- |
| 5 hrs. | 10 hrs. | 3 hrs. | 3 hrs | 12–16 hrs. | 3 hrs. |
| −40° C. | −15° C. | 0° C. | 20° C. | to 25° C. | 37° C. |

EXAMPLE 2

Preparation of Solution (R2)

The solution (R2) used for conversion of sucrose to glucose and then to 6-phosphogluconate was prepared from the 7.5 liters of solution reserved during the preparation of solution R1, as described in Example 1.

To this reserved solution was added 4,800,000 units of the enzyme invertase. The resulting solution was used to fill 10 ml glass vials with 1.50–1.55 ml of solution each. The vials were lyophilized at 200 millitorr, using the temperature program described in Example 1.

EXAMPLE 3

Preparation of Standards and Controls (a) Preparation of a Sucrose Standard.

A sucrose standard was prepared by adding sucrose to water to form a solution with a sucrose concentration of 1.0 mmol/L (34.2 mg/dL).

Two urine control samples (Urine Control I & II) were prepared.

(b) Preparation of Urine Control Level I (0.25 mM).

A sucrose stock solution was prepared by adding sucrose (3.423 g) to deionized water (50–75 ml) in a 100 ml flask containing a magnetic stir bar. The contents were mixed until the sucrose dissolved. The stir bar was removed and the contents diluted to 100 ml with deionized water. The stir bar was returned to the flask, and the contents mixed for 15–25 minutes.

The urine control sample was made by adding a measured amount of the sucrose stock solution to filtered human urine. The human urine had a sucrose concentration of 0.1 mM.

The amount of the sucrose stock solution was calculated according to the following formula:

$$1500 \text{ ml}/(100/(0.25-0.1))=2.25 \text{ ml}$$

The amount of the human urine was calculated as follows: 1500 ml−2.25 ml=1497.75 ml.

The calculated amounts of sucrose solution and human urine were added to a 2 liter beaker and mixed with a magnetic stir bar for 15 minutes. Boric acid (12.5 g) was added to the solution, the contents mixed until dissolved, and then mixed for an additional 30 minutes.

The urine control solution was dispensed into 5 ml glass vials in aliquots of 2.955–3.045 ml each. The vials were lyophilized to remove water.

(c) Preparation of Urine Control Level II (1.75 mM).

The sucrose stock solution from part (b) was used. The urine control sample was made by adding a measured amount of the sucrose stock solution to filtered human urine. The human urine had a sucrose concentration of 0.1 mM. The amount of the sucrose stock solution was calculated according to the following formula:

$$1500 \text{ ml}/(100/(1.75-0.1))=24.75 \text{ ml}$$

The amount of the human urine was calculated as follows: 1500 ml−24.75 ml=1475.25 ml.

The calculated amounts of sucrose solution and human urine were added to a 2 liter beaker and mixed with a magnetic stir bar for 15 minutes. Boric acid (12.5 g) was added to the solution, the contents mixed until dissolved, and then mixed for an additional 30 minutes.

The urine control solution was dispensed into 5 ml glass vials in aliquots of 2.955–3.045 ml each. The vials were lyophilized to remove water.

EXAMPLE 4

Determination of Sucrose in Urine —Two-Solution Method

A Hoffman LaRoche COBAS FARA II centrifugal clinical chemistry analyzer was used to determine the sucrose concentration in samples of human urine. The instrument was operated in sequential batch mode with a sample capability of 28 samples per cycle. One portion of the urine was analyzed for sucrose plus glucose, and a second portion for glucose only. The approximate assay time was 24 minutes for sucrose plus glucose, and 14 minutes for glucose.

Urine samples were stored frozen at −20° C. After thawing, the samples were clarified by removing suspended particles in a centrifuge at 5000 ×g for 15 minutes or by filtration through 0.8 micron filters.

Approximately 1 mL of the clarified urine was transferred into COBAS FARA sample cups and placed in the sample racks. All assays were performed at 37° C.

The sucrose plus glucose assay was carried out by parallel pipetting 10 $\mu$L of urine and 10 $\mu$L of distilled water wash into the assay cuvette with 20 $\mu$L of invertase followed by 10 $\mu$L of distilled water wash. This mixture was incubated for 10 min. and 260 $\mu$L of a solution containing co-factors was added to each cuvette. The reaction mixture was incubated for 3 min. to equilibrate the temperature to 37° C. and 2 $\mu$L of a hexokinase-G-6-PDH solution w as pipetted with 10 $\mu$L distilled water wash. The absorbance was monitored at 340 nm for 10 min. starting 0.5 sec. after addition of the last reagent and the difference in absorbance from the first reading and the last reading was calculated. The change in absorbance was multiplied by an assay factor to give the millimolar concentration. Each assay run was calibrated with a primary sucrose standard (5 mM) prepared from a primary stock (100 mM) dissolved in reagent grade distilled water utilizing reagent grade sucrose. The stock standard (100 mM) was prepared in a total volume of 1 liter using an analytical balance accurate to 1/10,000 g to weigh the sucrose crystals. The calibration standard was run in duplicate before the other samples to calculate a conversion factor based on the measured change in absorbance and the target concentration of the calibration standard.

The glucose assay was carried out in an identical manner except that the first incubation step with invertase was omitted and a glucose calibration standard was used to calibrate the assay.

The minimum detectable sucrose concentration in a urine sample spiked with sucrose was found to be 0.1 mM. The linearity of the assay was valid up to a concentration of 10 mM sucrose or glucose. Sucrose assay precision in urine over a three day interval with 10 assays per day done in two separate runs averaged less than a 5% coefficient of variation for urine samples containing either 2.5 mM sucrose (CV=4.7%, n=30) or 0.5 mM sucrose (CV=3.5%, n=30). Similar values of precision were achieved for glucose determinations in urine.

The sucrose recovery from urine is reported below as an average of four determinations at each level:

| Sucrose Level, mM | Recovery |
| --- | --- |
| 0.1 | 74% |
| 0.5 | 96% |
| 1.0 | 98% |
| 2.5 | 97% |
| 5.0 | 95% |
| 10.0 | 97% |

EXAMPLE 5

Determination of Sucrose in Urine—One-Solution Method

Samples were analyzed using the Hitachi 704 Automated Analyzer at 37° C. Approximately 500 μL of clear urine sample was transferred to sample cups. A sample of 0.85% saline solution was placed in the S1 sample cup for blanking purposes and a sample of 1.0 mM sucrose solution was placed in the S2 sample cup for calibration. The instrument was programmed to use 5 μL of urine sample, to which 360 μL of reagent R1 was added. Absorbance readings were made at a primary wavelength of 340 nm and a secondary wavelength of 376 nm. An initial absorbance measurement was taken after 5 minutes. Ninety μL of reagent R2 was added immediately after the 5 minute absorbance reading. The final absorbance reading was taken at 10 minutes.

Sucrose added to urine samples at levels of 0.5, 1.0 and 5.0 mmol/L, and recovery of sucrose from these samples was measured. Recoveries were 100.0%, 97.0% and 100.6% for the 0.5, 1.0 and 5.0 mmol/L samples, respectively. The average recovery was 99.2%.

The procedure was found to be linear to 20 mmol/L (685 mg/dL) of sucrose using an automated analyzer. If background glucose levels exceed 20 mmol/L (685 mg/dL), sucrose linearity will be reduced.

Within run precision was established by assaying two urine pools to which sucrose was added, with the following results:

| Sample | N | Mean mmol/L | Mean mg/dL | Std. Dev. mmol/L | Std. Dev. mg/dL | Coeff. Var. |
| --- | --- | --- | --- | --- | --- | --- |
| Pool 1 | 20 | 5.05 | 172.9 | 0.031 | 1.06 | 0.6% |
| Pool 2 | 20 | 0.50 | 17.1 | 0.006 | 0.21 | 1.2% |

Other variations and modifications of this invention will be obvious to those skilled in the art. This invention is not limited except as set forth in the claims.

What is claimed is:

1. A kit for use in a diagnostic method for detecting sucrose in blood or urine, said kit comprising:
   (a) a first container having therein a first reagent mixture comprising ATP, NAD, hexokinase, G-6-PDH, and a buffer, present in amounts effective to provide a first reagent solution comprising (i) ATP in a concentration in the range from about 0.5 mM to about 5.0 mM, (ii) NAD in a concentration in the range from about 0.5 mM to about 3.0 mM, (iii) hexokinase in a concentration in the range from about 200 U/L to about 2000 U/L, and (iv) G-6-PDH in a concentration in the range from about 500 U/L to about 2500 U/L, the first reagent solution having a pH in the range from about 7 to about 8;
   (b) a second container having therein a second reagent mixture comprising ATP, NAD, hexokinase, G-6-PDH, invertase, and a buffer, present in amounts effective to provide a second reagent solution comprising (i) ATP in a concentration in the range from about 0.0 mM to about 5.0 mM, (ii) NAD in a concentration in the range from about 0.0 mM to about 3.0 mM, (iii) hexokinase in a concentration in the range from about 0 U/L to about 2000 U/L, (iv) G-6-PDH in a concentration in the range from about 0 U/L to about 2500 U/L, and (v) invertase in a concentration in the range from about 0 U/L to about 2500 U/L, and (v) invertase in a concentration in the range from about 50 kU/L to about 500 kU/L, the second reagent solution having a pH in the range from about 7 to about 8; and
   (c) a third container having a sucrose solution as a standard and a preservative;
   wherein said kit is stable when stored or transported.

2. The kit of claim 1, wherein the first and second reagent mixtures are solids suitable for reconstitution.

3. The kit of claim 2 wherein the sucrose concentration of said solution in said third container is from about 0.1 mM to about 5 mM.

4. The kit of claim 3 further comprising at least one container having therein a solid control derived from lyophilization of an aqueous solution containing human urine, sucrose, and a preservative.

5. The kit of claim 4, wherein the preservative in the solid control is boric acid.

6. The kit of claim 5 further comprising at least one preservative in the first container and in the second container.

7. The kit of claim 6, wherein the at least one preservative in said first and second reagent solutions comprises sodium azide and gentamycin sulfate.

8. The kit of claim 7, further comprising a stabilizer in the first container and in the second container.

9. The kit of claim 8, wherein the stabilizer in said first and second reagent solutions is albumin.

10. The kit of claim 9, wherein said first reagent solution has a pH in the range from about 7.40 to about 7.55; and said second reagent solution has a pH in the range from about 7.40 to about 7.55.

11. The kit of claim 10, wherein said first reagent solution is comprised of (i) ATP in a concentration from about 1.0 mM to about 3.0 mM, (ii) NAD in a concentration from about 1.5 mM to about 2.5 mM, (iii) hexokinase in a concentration from about 500 U/L to about 1000 U/L, and (iv) G-6-PDH in a concentration from about 1000 U/L to about 2000 U/L, and the first reagent solution has a pH from about 7.40 to about 7.55; and said second reagent solution is comprised of (i) ATP in a concentration from about 1.0 mM to about 3.0 mM, (ii) NAD in a concentration of about 1.5 mM to about 2.5 mM, (iii) hexokinase in a concentration from about 500 U/L to about 1000 U/L, (iv) G-6-PDH in a concentration from about 1000 U/L to about 2000 U/L, and (v) invertase in a concentration from about 300 kU/L to about 400 kU/L, and the second reagent solution has a pH from about 7.40 to about 7.55.

* * * * *

UNITED STATES PATENT AND TRADEMARK OFFICE
CERTIFICATE OF CORRECTION

PATENT NO. : 6,270,725 B1
DATED : August 7, 2001
INVENTOR(S) : Alex D. Romaschin It is certified that error appears in the above-identified patent and that said Letters Patent is hereby corrected as shown below:

<u>Column 3,</u>
Line 15, "a s" should read -- as --;
Line 15, "herein ." should read -- herein. --; and
Line 27, "-1piperazineethanesulfonic" should read -- -1-piperazineethanesulfonic --.

<u>Column 4,</u>
Line 19, "a mount" should read -- amount --.

<u>Column 8,</u>
Line 64, "w as" should read -- was --.

Signed and Sealed this

Twenty-ninth Day of July, 2003

JAMES E. ROGAN
*Director of the United States Patent and Trademark Office*